United States Patent
Kiesele

[19]
[11] Patent Number: 5,855,750
[45] Date of Patent: Jan. 5, 1999

[54] ELECTROCHEMICAL MEASURING CELL FOR DETECTING OXIDIZING GASES

[75] Inventor: Herbert Kiesele, Lübeck, Germany

[73] Assignee: Drägerwerk AG, Lübeck, Germany

[21] Appl. No.: 796,514

[22] Filed: Feb. 6, 1997

[30] Foreign Application Priority Data

Sep. 25, 1996 [DE] Germany ............... 196 39 311.6

[51] Int. Cl.⁶ .................................................. G01N 27/26
[52] U.S. Cl. ........................ 204/415; 204/431; 204/432
[58] Field of Search ................... 204/415, 431, 204/432

[56] References Cited

U.S. PATENT DOCUMENTS 3,824,166  7/1974  Deibert ..................................... 204/432
5,234,567  8/1993  Hobbs et al. .......................... 204/415
5,624,546  4/1997  Milco ..................................... 204/415

FOREIGN PATENT DOCUMENTS

PS 15 52 620  9/1979  United Kingdom .

*Primary Examiner*—Bruce F. Bell
*Attorney, Agent, or Firm*—McGlew and Tuttle

[57] ABSTRACT

An electrochemical measuring cell for detecting oxidizing gases, containing an electrode with a redox mediator, which is oxidized by the gas to be detected. A measuring electrode is employed made of an inert material, and a counterelectrode is provided. The dynamics and reproducibility of the measured signal are improved by providing the counterelectrode formed of an anodically oxidizable material and is arranged behind the measuring electrode in the direction of diffusion in a sandwich-like arrangement.

18 Claims, 1 Drawing Sheet

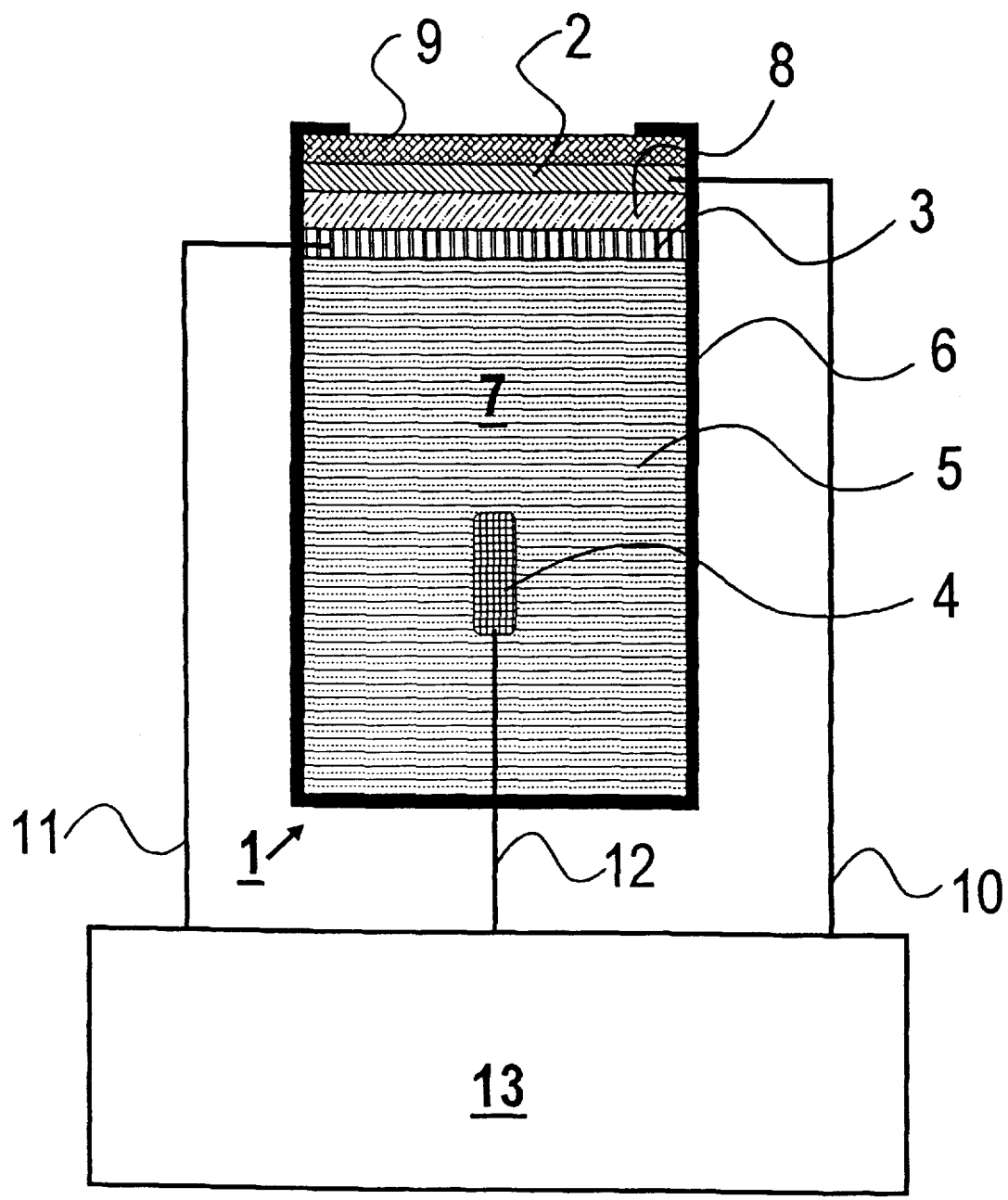

ELECTROCHEMICAL MEASURING CELL FOR DETECTING OXIDIZING GASES

FIELD OF THE INVENTION

The present invention pertains to an electrochemical measuring cell for detecting oxidizing gases, containing an electrolyte with a redox mediator, which is oxidized by the gas to be detected; a measuring electrode made of an inert material, and at least one additional electrode acting as a counterelectrode.

BACKGROUND OF THE INVENTION

An electrochemical measuring cell for detecting chlorine has become known from GB-PS 15 52 620. In the prior-art measuring cell, the measuring electrode and the counterelectrode consist of an inert material, e.g., platinum, and an electrolyte containing calcium bromide as the redox mediator is used. The redox mediator is oxidized by the chlorine to be detected at the measuring electrode, and the bromine formed in the process can be again reduced into $Br^-$ at the inert measuring electrode. However, it was found that the bromine formed during the oxidation of chlorine is not completely reacted at the measuring electrode, but it enters the electrolyte space and leads to memory effects. Bromine is formed from the bromide ions at the counterelectrode, and this bromine leads to the above-mentioned memory effects, on the one hand, and it interferes with the measuring electrode, on the other hand. The presence of bromine in the electrolyte leads to long rise and decay times of the measured signal, and no stable plateau value develops in the case of continuous exposure to chlorine.

SUMMARY AND OBJECTS OF THE INVENTION

The primary object of the present invention is to improve an electrochemical measuring cell of the above-described type in terms of the dynamics and reproducibility of the measured signal.

According to the invention, an electrochemical measuring cell is provided for detecting oxidizing gases. The measuring cell contains an electrolyte with a redox mediator, which is oxidized by the gas to be detected as well as a measuring electrode made of an inert material, and at least one additional electrode acting as a said counterelectrode. The counterelectrode comprises an anodically oxidizable material and is arranged behind the measuring electrode in the direction of diffusion in a sandwich-like arrangement.

The advantage of the present invention is essentially that an expendable anode consisting of an anodically oxidizable material is used as the counterelectrode, so that the corresponding metal ions are formed rather than bromine. It is especially advantageous for the metal ions to form a poorly soluble precipitate with the bromide ions, as it happens in the case of, e.g., silver. The breakthrough of chlorine and bromine into the electrolyte space is prevented from occurring by the sandwich-like arrangement of the measuring electrode and the counterelectrode, because the counterelectrode acts as a kind of chemical filter.

The chemical reactions taking place between the measuring electrode and a counterelectrode made of silver can be described by the following equations:

Reaction of chlorine with the redox mediator $Br^-$:

$$Cl_2 + 2\ Br^- \rightarrow 2Cl^- + Br_2$$

Measuring electrode:

$$Br_2 + 2e^- \rightarrow 2Br^-$$

Counterelectrode:

$$2Ag \rightarrow 2Ag^+ + 2e^-$$

Cell reaction:

$$Br_2 + 2Ag \rightarrow 2AgBr$$

Experiments have shown that a life of more than 50,000 ppm-hours can be reached with about one gram of silver at the counterelectrode.

The counterelectrode is advantageously grid-like or is designed as a sintered metal body and it covers the measuring electrode two-dimensionally. The transfer of chlorine or bromine or iodine into the electrolyte space is thus prevented from occurring in an especially effective manner, because the counterelectrode shields the measuring electrode from the electrolyte space over the entire surface.

The counterelectrode is preferably made of nickel, tin, lead, copper, silver, mercury, or alloys of these metals. The suitable materials for the measuring electrode include, e.g., a metal of the platinum group, or gold.

A reference electrode is advantageously arranged in the electrolyte space at a sufficient distance from the measuring and counterelectrode. An especially stable potential can be set at the measuring or counterelectrode with the reference electrode, because the potential of the reference electrode is changed by bromine only insignificantly due to the spaced location from the measuring and counterelectrodes.

Silver/silver bromide, iridium/iridium oxide, or platinum/platinum oxide are especially suitable materials for the reference electrode.

An electrolyte-permeable separator, with which an especially short distance can be set between the measuring electrode and the counterelectrode, is preferably arranged between the measuring electrode and the counterelectrode. Favorable values are obtained in the case of distances of, e.g., 0.1 mm to about 1 mm.

The redox mediator is advantageously selected from the group of the bromides and iodides of alkali and alkaline earth metals, or tetraalkylammonium salts. The preferred redox mediators are lithium bromide, magnesium bromide, or calcium bromide.

The measuring cell according to the present invention is especially suitable for detecting $Cl_2$, $NO_2$, $H_2O_2$, and $O_3$.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a partially schematic perspective view of a measuring cell according to the invention.

DESCRIPTION OF THE PREFERRED EMBODIMENT

Referring to the drawings in particular, the only FIGURE shows an electrochemical measuring cell 1 for detecting chlorine, with a measuring electrode 2 made of gold, a counterelectrode 3 made of a silver mesh, and a reference electrode 4 made of sintered silver powder, which are arranged in an electrolyte space 5 of a measuring cell housing 6. The electrolyte space 5 is filled with an aqueous electrolyte 7 consisting of lithium bromide (6M), which also acts as the redox mediator at the same time. A separator 8 made of glass mat with a thickness of 0.3 mm is located between the measuring electrode 2 and the counterelectrode 3 in order to set a uniform distance between the electrodes 2, 3. The reference electrode 4 is fastened at a distance of a few mm from the electrodes 2, 3, so that its potential cannot be influenced by bromine. The measuring cell housing 6 is closed off from the environment at the measuring electrode 2 with a diaphragm 9, through which chlorine is able to diffuse to the measuring electrode 2 (in a diffusion direction). The measuring electrode 2, the counterelectrode 3, and the reference electrode 4 have measuring connections 10, 11, 12, which are led through the measuring cell housing 6 and are connected to an evaluating circuit 13 with a potentiostat, not shown in the FIGURE.

The mode of operation of the measuring cell according to the present invention is as follows: When chlorine gas is admitted to the diaphragm 9, chlorine diffuses through the measuring electrode 2 and into the electrolyte 7, and it oxidizes the redox mediator, lithium bromide, there. The bromine formed in this process is reduced again into $Br^-$ at the measuring electrode 2, and the bromine molecules not reacted at the measuring electrode 2 are captured at the counterelectrode 3, and they react with the electrode material to form silver bromide there. The reference electrode 4 made of silver supplies a stable potential, because it is located protected behind the counterelectrode 3 and is not compromised by bromine molecules. The long-term stability and the reproducibility of the measuring cell 1 according to the present invention are further improved by the reference electrode 4.

While specific embodiments of the invention have been shown and described in detail to illustrate the application of the principles of the invention, it will be understood that the invention may be embodied otherwise without departing from such principles.

What is claimed is:

1. An electrochemical measuring cell for detecting oxidizing gases, comprising:
   a container with an opening defining a direction of diffusion into the container;
   an electrolyte disposed in the container with a redox mediator, which is oxidized by the gas to be detected;
   a measuring electrode disposed in the container, said measuring electrode being made of an inert material; and
   at least one additional electrode acting as a counterelectrode, said counterelectrode comprising an anodically oxidizable material and being arranged behind said measuring electrode in said direction of diffusion in a sandwich arrangement.

2. An electrochemical measuring cell in accordance with claim 1, wherein said counterelectrode is permeable to said electrolyte.

3. An electrochemical measuring cell in accordance with claim 2, wherein said counterelectrode is a grid.

4. An electrochemical measuring cell in accordance with claim 2, wherein said counterelectrode is a perforated plate.

5. An electrochemical measuring cell in accordance with claim 2, wherein said counterelectrode is a sintered metal body.

6. An electrochemical measuring cell in accordance with claim 1, wherein said measuring electrode comprises metal of the platinum group or gold, and said counterelectrode is selected from the group of materials consisting of nickel, tin, lead, copper, silver, mercury and alloys of these metals.

7. An electrochemical measuring cell in accordance with claim 1, further comprising a reference electrode provided as an additional electrode.

8. An electrochemical measuring cell in accordance with claim 7, wherein said reference electrode is selected from the group consisting of silver/silver bromide, iridium/iridium oxide, and platinum/platinum oxide.

9. An electrochemical measuring cell in accordance with claim 1, wherein a separator impregnated with electrolyte is present between said measuring electrode and said counterelectrode.

10. An electrochemical measuring cell in accordance with claim 1, wherein said redox mediator is selected from the group consisting of the bromides and iodides of alkali and alkaline earth metals, and corresponding tetraalkylammonium salts.

11. An electrochemical measuring cell in accordance with claim 1, wherein said redox mediator is one of lithium bromide, magnesium bromide, and calcium bromide.

12. An electrochemical measuring cell in accordance with claim 1, wherein the electrolyte and redox mediator detect one or more of $Cl_2$, $Br_2$, $NO_2$, $H_2O_2$, and $O_3$.

13. An electrochemical measuring cell for detecting oxidizing gases, comprising:
   a container with an opening defining a direction of diffusion into the container;
   an electrolyte disposed in the container with a redox mediator, which is oxidized by the gas to be detected;
   a measuring electrode disposed in the container, said measuring electrode being made of an inert material;
   at least one additional electrode as a counterelectrode, said counterelectrode comprising an anodically oxidizable material permeable to said electrolyte;
   a separator impregnated with electrolyte, said counterelectrode being arranged behind said measuring electrode in said direction of diffusion in a sandwich arrangement with said separator present between said measuring electrode and said counterelectrode; and
   a reference electrode provided as an additional electrode.

14. An electrochemical measuring cell in accordance with claim 13, wherein said counterelectrode is selected from the group consisting of a grid, a perforated plate and a sintered metal body.

15. An electrochemical measuring cell in accordance with claim 13, wherein said measuring electrode comprises metal of the platinum group or gold, and said counterelectrode is selected from the group of materials consisting of nickel, tin, lead, copper, silver, mercury and alloys of these metals.

16. An electrochemical measuring cell in accordance with claim 13, wherein said reference electrode is selected from the group consisting of silver/silver bromide, iridium/iridium oxide, and platinum/platinum oxide.

17. An electrochemical measuring cell in accordance with claim 13, wherein said redox mediator is selected from the group consisting of the bromides and iodides of alkali and alkaline earth metals, and corresponding tetraalkylammonium salts.

18. An electrochemical measuring cell in accordance with claim 13, wherein said redox mediator is one of lithium bromide, magnesium bromide, and calcium bromide.

* * * * *